(12) United States Patent
Tang (10) Patent No.: US 10,883,983 B2
(45) Date of Patent: Jan. 5, 2021

(54) BIOSENSORS COMPRISING A GATE-KEEPER MEMBRANE

(71) Applicant: LeNano Diagnostics Inc., Mississauga (CA)

(72) Inventor: Xiaowu Tang, Waterloo (CA)

(73) Assignee: LeNano Diagnostics Inc., Mississauga (CA)

( * ) Notice: Subject to any disclaimer, the term of this patent is extended or adjusted under 35 U.S.C. 154(b) by 346 days.

(21) Appl. No.: 15/290,505

(22) Filed: Oct. 11, 2016

(65) Prior Publication Data

US 2017/0307602 A1 Oct. 26, 2017

(30) Foreign Application Priority Data

Apr. 26, 2016 (CN) .......................... 2016 1 0266687

(51) Int. Cl.
*G01N 33/543* (2006.01)
*G01N 27/327* (2006.01)

(52) U.S. Cl.
CPC ... *G01N 33/54373* (2013.01); *G01N 27/3271* (2013.01); *G01N 33/54306* (2013.01)

(58) Field of Classification Search
CPC ....... G01N 33/54373; G01N 33/54306; G01N 27/3271
See application file for complete search history.

(56) References Cited

U.S. PATENT DOCUMENTS

| | | | |
|---|---|---|---|
| 7,611,628 B1 | 11/2009 | Hinds, III | |
| 8,940,173 B2 | 1/2015 | Bakajin et al. | |
| 9,291,613 B2 | 3/2016 | Bryant et al. | |
| 2002/0121235 A1* | 9/2002 | Carpenter | G01N 21/293 116/206 |
| 2007/0052045 A1* | 3/2007 | Arora | B81C 1/00007 257/414 |
| 2009/0283475 A1 | 11/2009 | Hylton et al. | |
| 2011/0220574 A1 | 9/2011 | Bakajin et al. | |
| 2011/0253630 A1 | 10/2011 | Bakajin et al. | |

(Continued)

OTHER PUBLICATIONS

Siwy, Zuzanna, et al. "Protein biosensors based on biofunctionalized conical gold nanotubes." Journal of the American Chemical Society 127.14 (2005): 5000-5001.*

(Continued)

*Primary Examiner* — Robert J Eom
(74) *Attorney, Agent, or Firm* — Susan Tandan; Gowling WLG (Canada) LLP (57) ABSTRACT

A device for the detection of a target analyte in solution is provided. The device comprises a gate-keeper membrane made of a substrate having a first receptor surface for exposure to the target analyte and a second opposing surface exposed to a detector, wherein the substrate is adapted to incorporate pores sufficient to permit passage of a reporter through the membrane from exposure to the first receptor surface to the second opposing surface; one or more receptors anchored on the first surface of the substrate which bind with the target analyte, wherein binding of the receptor with the target analyte alters the passage of the reporter through the pores of the membrane; and one or more detectors which interact with reporter that passes through the membrane and emits a detectable signal that permits quantification of reporter in the detection reservoir.

17 Claims, 8 Drawing Sheets

(56) References Cited

U.S. PATENT DOCUMENTS

2011/0257033 A1    10/2011  Strano et al.
2012/0114089 A1*    5/2012  Potyrailo ............. G21C 17/022
                                                        376/247
2014/0197046 A1     7/2014  Busnaina et al.
2014/0209539 A1     7/2014  El Badawi et al.

OTHER PUBLICATIONS

Nednoor et al.: "Carbon nanotube based biomimetic membranes: mimicking protein channels regulated by phosphorylation", J. Mater. Chem. 2007, 17 (18), pp. 1755-1757.
Nednoor et al.: "Reversible biochemical switching of ionic transport through aligned carbon nanotube membranes", Chem. Mater. 2005, 17 (14), pp. 3595-3599.
Mazloumi et al.: "Fabrication of three-dimensional carbon nanotube and metal oxide hybrid mesoporous architectures", ACS Nano 2013, 7 (5), pp. 4281-4288.

* cited by examiner

BIOSENSORS COMPRISING A GATE-KEEPER MEMBRANE

FIELD OF INVENTION

The present invention generally relates to a device, method, and membrane for the identification and quantification of an analyte in solution, and more particularly relates to a nano-biosensor.

BACKGROUND

Electrochemical biosensors provide a means to analyze the content of a biological sample by direct conversion of a biological event to an electrical signal. They are highly sought-after due to their great potential for miniaturization and integration into low-cost and portable systems that have a broad spectrum of significant applications including disease diagnostics, food safety monitoring, and environmental pollution detection.

Devices incorporating such biosensors have been developed in the past, including for example, devices using electrodes (e.g. cyclic voltammetry, chronoamperometry, impedance spectroscopy, etc.), and field effect transistors (FETs), and more recently, nanoelectronic devices incorporating nanowire/nanotube (NW/NT) sensors. Electrochemical biosensors generally suffer from a lack of high sensitivity and specificity towards a desired biochemical event, and thus, are not capable of providing early detection of biomarkers in body fluids for disease diagnostics or the detection of trace amounts of contaminants in water, meat, air, etc., unless extensive sample preparation steps are conducted.

Nanomaterials typically possess an extremely high surface-volume ratio and can be functionalized for sensing various target analytes. However, despite this, current biosensors using nanomaterial-based transducers do not exhibit high sensitivity and low detection limits generally achievable by the intrinsic nanomaterial properties. Thus, while nano-electronic sensory devices have shown promise to provide improved sensitivity and arrayability, the technology for constructing practical nanoelectronic biosensors is still in its infancy. It remains challenging to achieve high sensitivity, specificity, and reproducibility simultaneously using existing electrochemical biosensors.

It is desirable, therefore, to provide new devices and methods to address one or more of the shortcomings of current electrochemical biosensors.

SUMMARY OF THE INVENTION

It has now been determined by the inventors that the sensor properties of current electrochemical biosensors may be diminished by direct interaction of the nanomaterial detector or transducer with the sensing receptors, for example, large molecular weight protein and nucleic acid sensing receptors. A novel device is herein provided comprising two interfaced components, namely, a gate-keeper membrane and a detector/transducer. The membrane comprises a receptor/passivation layer comprising sensing receptors for recognition of target analytes which is separated from the detector/transducer, and thus prevents or minimizes degradation of the detector/transducer and loss of sensitivity.

Thus, one aspect of the invention relates to a device for the detection of a target analyte in a sample solution. The device comprises: a gate-keeper membrane which allows passage of a reporter species; and a detector for detecting the amount/rate of reporter species that passes through the membrane. The gate-keeper membrane comprises a substrate with pores for the reporter species to pass through; and receptors anchored on the substrate which bind specifically to the target analyte, wherein said binding results in a change in the rate of passage or translocation of the reporter species through the membrane.

In another aspect, a gate-keeper membrane is provided comprising a substrate having a first receptor surface and a second opposing surface, wherein the substrate comprises pores sufficient to permit passage of a reporter species through the membrane and the first surface comprises receptors anchored in the substrate which bind specifically to a target analyte, wherein said binding alters the rate of passage of the reporter species through the membrane.

In another aspect, a device for the detection of a target analyte in solution is provided comprising:
a gate-keeper membrane within an enclosure, wherein the membrane comprises a substrate having a first receptor surface exposed to a sample reservoir in the enclosure and a second opposing surface exposed to a detection reservoir in the enclosure, wherein the substrate comprises pores sufficient to permit passage of a reporter through the membrane from the sample reservoir to the detection reservoir;
one or more receptors anchored within the first surface of the substrate which bind with the target analyte, wherein binding of the receptor with the target analyte alters the passage of the reporter through the membrane; and
one or more detectors within the detection reservoir which interact with reporter that passes through the membrane and emit a detectable signal that permits quantification of reporter in the detection reservoir.

These and other aspects of the invention are described in the detailed description that follows by reference to the following drawings.

DETAILED DESCRIPTION OF THE INVENTION

A device for the detection of a target analyte, for example, biomolecules such as nucleic acids and proteins, viruses, bacteria, fungi, and the like, in a solution is provided. As demonstrated in the examples provided herein, in one embodiment, the device comprises: an enclosure; and a gate-keeper membrane, which is within the enclosure, and divides the enclosure into two compartments: a sample reservoir and a detection reservoir. Analyte-specific receptors are anchored on the gate-keeper membrane on a first surface of the membrane which is exposed to the sample reservoir. A detector/transducer is located within the detection reservoir. Thus, target analytes and other macromolecules contained in a sample solution within the sample reservoir, as well as the receptors and passivation molecules exposed only to the sample reservoir, are not in direct contact with the detector/transducer and degradation of the detector is prevented, or at least minimized, to maintain the sensitivity of the detector.

The gate-keeper membrane within the enclosure divides the enclosure into a sample reservoir and a detection reservoir. Thus, the enclosure is not particularly restricted, and may be any enclosure suitable to receive the gate-keeper membrane and form the sample and detection reservoirs. The enclosure may be made of any inert material, including for example, plastics, glass, metal and the like. The enclosure of the device may include an inlet or other means for filling the sample reservoir with sample, and an outlet in the detection reservoir for emptying the contents therein. The inlet and outlet may include removable covers that function to seal the inlet/outlet opening to prevent leakage of the sample from the reservoirs.

The gate-keeper membrane comprises a substrate having a first receptor surface which is exposed to the sample reservoir in the enclosure and a second opposing surface which is exposed to the detection reservoir in the enclosure. The gate-keeper membrane comprises a matrix substrate material, examples of which include but are not limited to, polydimethylsiloxane (PDMS), expoxy, polyethylene glycol (PEG), hydroxypropyl cellulose (HPC), poly(N-isopropylacrylamide), silica nanoparticles, iron oxide nanoparticles, and alumina nanoparticles.

Disposed within the membrane substrate is a material that forms pores, e.g. nanoscale or microscale pores, through which only a reporter species (e.g. small molecules, ions) and water molecules can pass, but which does not permit passage of larger analyte molecules. The pores are formed to extend from the first surface to the second opposing surface (e.g. the surface on the opposite side of the membrane to the first surface) of the substrate to permit passage of reporter species through the membrane from the sample reservoir to the detection reservoir. The pores are formed by nano- or micro-materials preferably having a high surface area and light weight. Examples of suitable nano- or micro-materials include, but are not limited to, carbon nanotubes, graphene, and graphene oxide. The density of pores within the membrane is not critical. The membrane may include a single pore or a high density of pores. In some embodiments of the invention, the pore density within a gate-keeper membrane is in the order of 10M to 100M/mm$^2$. The membrane substrate functions to bind the nano- or micro-material together to form a porous membrane of high integrity.

In one embodiment, the gate-keeper membrane substrate incorporates semi-aligned carbon nanotubes (e.g. in the form of cylindrical pipes) which are oriented perpendicular to the membrane surface. In this configuration, the reporter species pass through the inner core of the nanotubes. The intrinsic inner core of the semi-aligned carbon nanotubes forms nano-sized channels or pores, e.g. 1-5 nm in diameter, through which a reporter species can pass for detection by the detector/transducer in the detection reservoir. In another embodiment, the carbon nanotubes, e.g. in the form of long flexible polymer fibers, are woven into a mat which is oriented parallel to the membrane surface. Within the mat, tube orientation is random. In this configuration, the reporter species go through the inter-tube spaces of the fibers. In the case of the randomly oriented carbon nanotubes, the inter-tube spaces form nano-sized pores for the reporter species to pass through. The pore size can be readily varied by varying tube density and membrane substrate material. One example of a gatekeeper membrane comprises semi-aligned carbon nanotubes and PDMS as the substrate material. Both ends of the carbon nanotubes are open. Another example of a membrane comprises stacked graphene or graphene oxide platelets which are formed into a membrane through vacuum filtration of graphene or graphene oxide solutions. Fillers can be used, such as PEG, HPC, poly(N-isopropylacrylamide), silica nanoparticles, iron oxide nanoparticles, and alumina nanoparticles, which are mixed with the graphene or graphene oxide solutions prior to filtration to make hybrid or smart substrates.

The gate-keeper membrane may include an additional supporting layer to improve the mechanical strength of the membrane, which makes the membrane easier to handle and prevents potential damage to the membrane during handling, transport, and use for analyte measurements. The supporting layer generally comprises pores that are larger than the pores within the gate-keeper membrane to provide mechanical support while not blocking the membrane pores. Examples of materials suitable for use as such a supporting layer include, but are not limited to, porous silicon nitride or filter membrane such as paper, polycarbonate, or alumina membranes.

Additionally, the device may include an isolation or protective layer which partially or completely covers the gate-keeper membrane surface (including the pores) to protect the membrane, for example, from environmental contamination. This protective layer is a removable layer which is removed before use of the device. Examples of materials suitable for use as the protective layer include materials that are readily removable from the device such as a thin film of gold which is removable by applying an electric potential, or a thin polymer layer readily removed by dissolving in water.

The gate-keeper membrane may be made using methods generally known to those of skill in the art. For example, the nanomaterials may be embedded within the membrane substrate and cured to form the porous gate-keeper membrane at a suitable curing temperature for a sufficient period of time. Excess substrate may then be removed using methods such as wet-etching and plasma oxidation. Supporting and/or isolation layers may be coated onto the membrane using well-established techniques.

One or more selected receptors are anchored onto the first surface of the gate-keeper membrane substrate. Receptors are selected for their specificity to bind with a target analyte. Examples of molecules that may be used as receptors include nucleic acid (e.g. ssDNA or RNA), aptamers, antibodies, peptides, enzymes, and other entities that exhibit binding specificity with a potential target analyte. Anchoring of receptors on the membrane may be achieved by various methods including covalent linkage, electrostatic attraction, ionic bonding, hydrogen bonding, or van der Waals' forces. Thus, the strength of receptor-membrane substrate binding may be varied (e.g. strong or weak) with the anchoring method used. The anchoring method may vary with the target analyte such that a change occurs on receptor-analyte binding that alters that passage of reporter species through the membrane. For example, if the receptors used in the device are large molecules which effectively block the pores in the membrane, weaker forces such as vdW, may be used to anchor the receptors to the membrane. Subsequent receptor-analyte binding which is stronger than the vdW forces anchoring the receptor on the membrane, then results in release of the receptors from the membrane, unblocking of the pores and an increase in the rate of passage of reporter through the membrane from the sample reservoir to the detection reservoir. Alternatively, if the target analyte molecules are large molecules, then the receptors may be anchored to the membrane by covalent linkage, and subsequent receptor-analyte binding will result in blocking of the membrane pores (by steric hindrance) when the large analyte molecules bind to the receptors. This binding variability is useful to broaden the range of applications of the present device.

The sample reservoir is adapted to retain a sample solution to be analyzed for the presence of a target analyte. The sample solution may be any solution including aqueous solutions such as water samples, aqueous extracts from various sample types such as foods, plants, soil, etc., and bodily fluid samples such as blood, plasma, serum, saliva, urine, tears, breast milk, cerebrospinal fluid, amniotic fluid and ascitic fluid. A selected reporter species may be added to the sample solution for detection of the target analyte as will be described, or may already be present within the sample solution. Generally, the reporter species is added to the sample solution in an amount that is greater than the amount of target analyte in the sample solution, e.g. an amount greater than picomolar-nanomolar amounts, for example, the reporter species may be in millimolar amounts.

The device includes one or more detectors within the detection reservoir which interacts with a reporter species that passes through the gate-keeper membrane to emit a detectable signal that permits quantification of the reporter species in the detection reservoir. Suitable reporter species, thus, include chemical entities that induce a detectable measurable change within the detection reservoir. The detection reservoir may include an inert solution, e.g. water, or may include a solution that facilitates detection of the reporter species.

Figure 8:
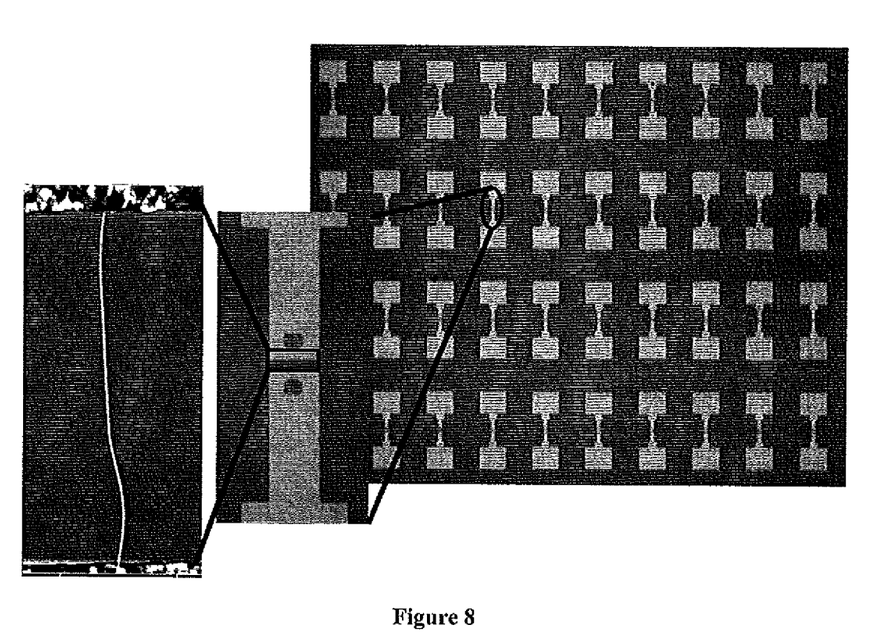
FIG. 8 shows an exemplary array of carbon nanotube chemiresistors.
Figure 9:
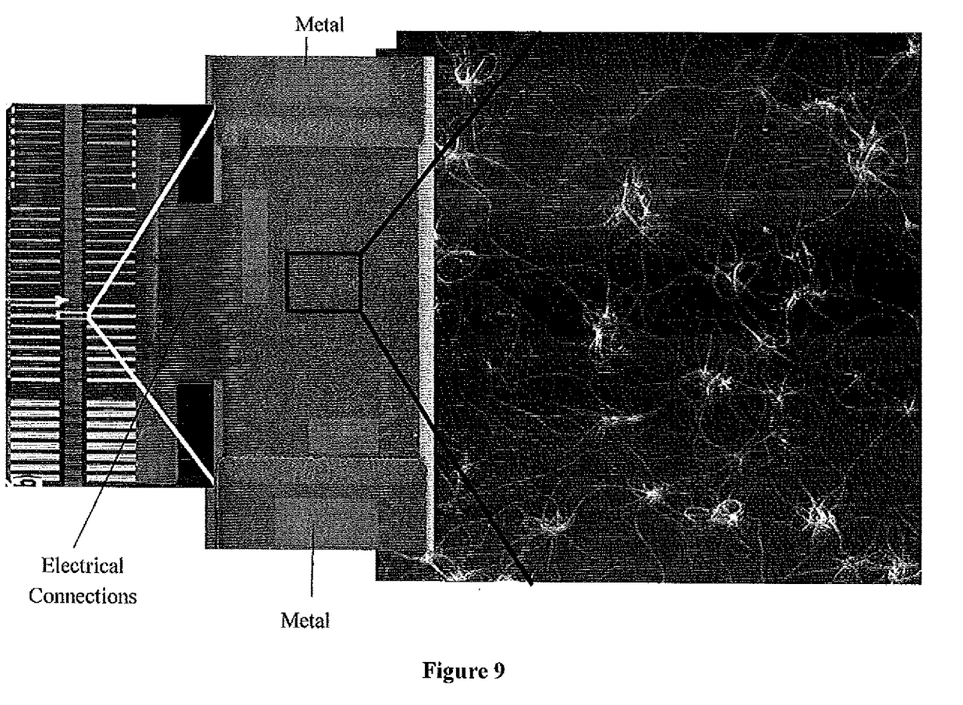
FIG. 9 shows another exemplary array of carbon nanotube network chemiresistors.

In one embodiment, the presence of the reporter species is detected electrochemically. Thus, the detector is a transducer which converts a physical property (e.g. concentration, pH, electrical charge, and the like) into an electrical signal, e.g. current, voltage, potential, and impedance. The transducer detector comprises an electrical sensory circuit which may optionally be mounted within the detection reservoir, for example, on a supporting substrate, on a surface of the enclosure or directly on the second surface of the gatekeeper membrane. The electrical sensory circuit may comprise, for example, two or more microelectrodes, one or more field effect transistors (FET)(s), or one or more carbon nanotube chemiresistors, e.g. comprising one or a network of single-walled carbon nanotubes bridging two metal contacts as shown in FIGS. 8 and 9. Carbon nanotube chemiresistors offer high sensitivity and small size, thus one or an array of chemiresistors can be used to improve specificity or achieve multiplexed detection. The microelectrodes for use may be metal (e.g. gold or platinum) or carbon electrodes, including working, counter, and reference electrodes. The electrodes may also be modified to include gold or carbon nano-/micro-particle deposits on the smooth electrode surface to improve sensitivity and specific surface area. The FET may be a Junction FET, a Metal Semiconductor FET, or a MOS FET. The detection reservoir may include an electrolyte solution to facilitate electrochemical detection of the reporter species. The electrolyte may be in the form of a layer between the gate-keeper membrane and the transducer.

The circuit emits a detectable electrical signal in response to the amount of reporter species in the detection reservoir, e.g. the amount of reporter species that passes through the gatekeeper membrane into the detection reservoir from the sample reservoir. The electrical signal may be electrical current, voltage, potential, or impedance (including capacitance, resistance, and inductance). Thus, various transducers may be used. Examples of reporter species for electrochemical detection using a transducer include, but are not limited to, mobile ions (e.g. H+, OH—, $Ca^{2+}$), redox species (e.g. $[Fe(CN)_6]^{3-}$, $[Ru(bipyridine)_3]^{2+}$), oxidizing agents (e.g. $[MnO_4]^-$, $O_2^{2-}$), reducing agents (e.g. vitamin C), and the like, which can induce a pH change, a chemical reaction, doping, or redox events, on the transducer surface which is then converted by the transducer into an electrical signal that can be measured.

The present device is useful in a method of sensing a single or multiple target analyte(s) in a solution, e.g. an aqueous solution. The detection of an analyte in solution may be conducted as follows. A sample solution is obtained and added to the sample reservoir of the present device. The sample solution may naturally include a reporter species. Alternatively, a selected reporter species is added to the sample solution in a sufficient amount, either prior to or subsequent to adding the sample solution to the sample reservoir. The sample solution is, thus, exposed to the first receptor surface of the gate-keeper membrane in the device. The presence of reporter species in the detection reservoir is monitored by the detector in the detection reservoir, e.g. by detecting and analyzing an electrical signal emitted from an electrochemical transducer in the detection reservoir in response to the amount of reporter species that passes through the membrane from the sample reservoir into the detection reservoir. Detection of a change in the amount of reporter species over time indicates the presence of target analyte in the sample solution which binds to receptor on the surface of the membrane to result in a change in the amount of reporter species that passes through the membrane. The amount of target analyte(s) in the sample solution is quantified based on the amount of reporter that passes through the membrane from the sample reservoir to the detection reservoir, since the amount of target analyte correlates with the change in the amount of reporter species that passes through the gate-keeper membrane.

As one of skill in the art will appreciate, the amount of reporter species that passes through the membrane may either increase or decrease in the presence of a target analyte. In one embodiment, the amount of the reporter species that passes through the gate-keeper membrane increases in the presence of a target analyte. This occurs when binding of the analyte to the receptor on the gate-keeper membrane causes release of the receptor from the membrane, and results in opening or exposure of the pores on the membrane to permit reporter to flow through the pores into the detection reservoir. Examples of receptors which release or expose the membrane pores on binding to target analyte include an aptamer receptor having a certain conformation, e.g. hairpin conformation, that blocks membrane pores. Binding to a heavy metal ion, such as lead (II) or mercury (II), results in a conformational change in the aptamer, e.g. straightening, which results in unblocking of membrane pores. Antibody-antigen binding is another example wherein a weakly bound antigen or antibody receptor block membrane pores. Membrane pores are exposed when the corresponding antibody or antigen, respectively, binds thereto and results in release of the antigen or antibody receptor from the membrane.

In another embodiment, the amount of the reporter species that passes through the gate-keeper membrane decreases in the presence of a target analyte. This occurs when binding of the analyte to the receptor on the gate-keeper membrane blocks the membrane pores, and therefore, blocks the flow of the reporter species through the pores into the detection reservoir. Examples in which receptor-analyte binding blocks the membrane pores include DNA hybridization in which a single DNA strand (receptor) binds or hybridizes with its corresponding DNA strand (analyte) to block membrane pores and prevent flow of reporter species through the pores. Antibody-antigen binding is another example wherein one of an antigen or antibody is the receptor which is strongly bound to the membrane. Membrane pores are blocked when its corresponding antibody or antigen, respectively, binds thereto, by steric hindrance.

Another aspect of the present invention relates to a gate-keeper membrane for use in a device to detect a target analyte in a sample solution. The gate-keeper membrane consists of a substrate with nano- or micro-scale pores for a reporter species, e.g. ion or small molecule, to pass through. Analyte-specific receptors are anchored on a first surface of the membrane substrate which can specifically bind to one or multiple target analytes. Receptor-analyte binding modulates or alters the rate at which the reporter species flows through the membrane.

EMBODIMENTS OF INVENTION

Figure 1:
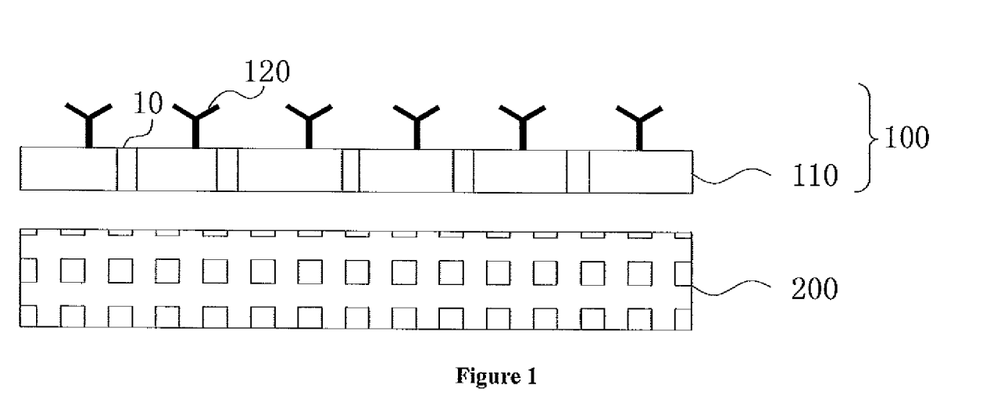
FIG. 1 is a schematic diagram of an exemplary device configuration in accordance with an embodiment of the invention.

One aspect of the invention relates to a device for the detection of target analytes in a sample solution, as shown in FIG. 1. The device comprises: a gate-keeper membrane (100) which allows reporter species to pass through; and a detector/transducer (200) for detecting the amount/rate of reporter species that passes through the membrane.

The gate-keeper membrane (100) comprises a substrate (110) within which are formed pores (10) which permit passage of a reporter species through the membrane (100). In addition, receptors (120) are bound to the surface of the substrate (110) which specifically bind to a target analyte to result in a change in the rate at which the reporter species passes through the pores (10) of the membrane (100). The rate of passage of the reporter species through the pores of the membrane correlates with the concentration of target analyte in the sample solution. Thus, the amount of reporter species that passes through the membrane pores into a detection reservoir is detected by a detector (200) over time and is used to calculate the analyte concentration in the sample solution.

Figure 2:
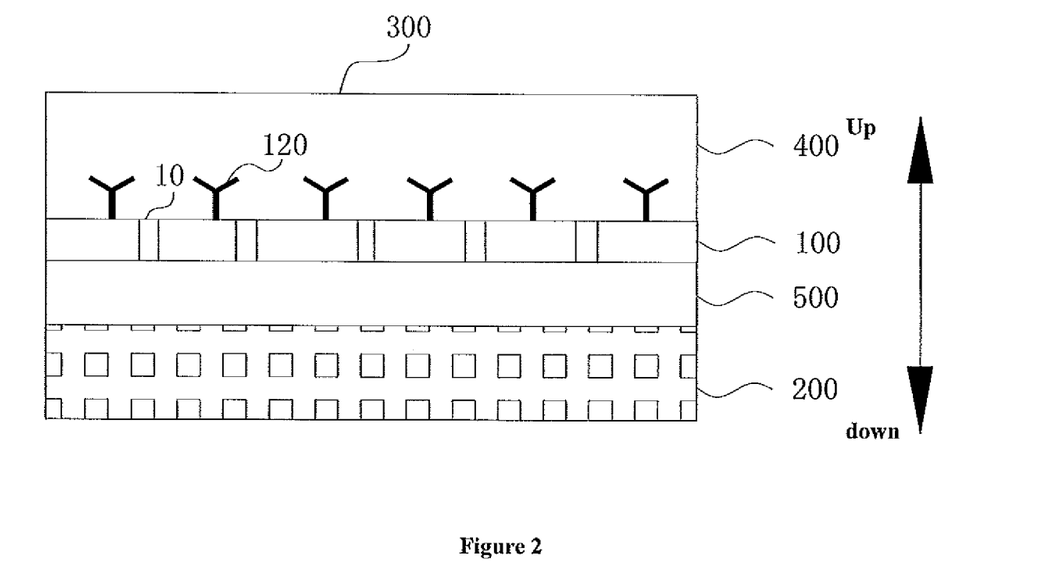
FIG. 2 is a schematic diagram of an exemplary device configuration in accordance with another embodiment of the invention.

As shown in FIG. 2, the device may include: an enclosure (300) which is divided by the membrane (100) into a sample reservoir (400) and a detection reservoir (500). The receptors (120) are bound to a first surface (40) of the membrane (100) which is situated in or exposed to the sample reservoir (400). The detector (200) for detecting or sensing reporter species is situated within the detection reservoir (500) which is exposed to a second surface (30) of the membrane. An analyte sample is placed in the sample reservoir (400), and either already includes or has added thereto a reporter species that can pass through pores in the membrane. If a target analyte is present in the sample, the receptors (120) will bind with the analyte and alter the rate at which the reporter species passes through the membrane (100) from the sample reservoir (400) into the detection reservoir (500). Reporter that passes through the membrane (100) is detected by a detector, for example, by generating an electrical signal.

Figure 3:
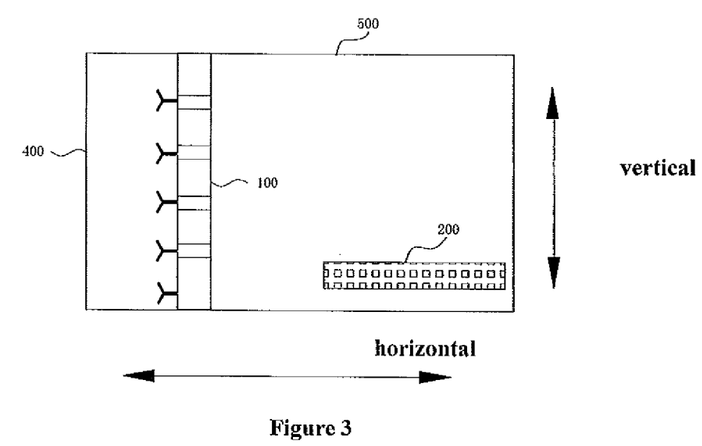
FIG. 3 is a schematic diagram of an exemplary device configuration in accordance with another embodiment of the invention.

The placement of the membrane (100) with respect to the detector is not particularly restricted as long as the first surface (40) of the membrane (100) comprising receptors (120) is within the sample reservoir (400) and the detector is within the detection reservoir (500). In one embodiment, as shown in FIG. 2, the membrane (100) is horizontal within the enclosure (300), the receptors (120) are on the top side of the membrane (100) and the detector (200) is underneath the membrane (100). An electrolyte may be present in between the membrane (100) and the detector (200). The reporter species pass through the pores (10) on the membrane (100) into the electrolyte in the detection reservoir (500) for detection by the detector (200). In another embodiment, as shown in FIG. 3, the membrane (100) is placed vertically within the sample reservoir (400) and the detector (200) is either horizontally placed (as shown) or vertically placed within the detection reservoir (500). The specific configuration and detector type is selected accordingly.

Figure 4:
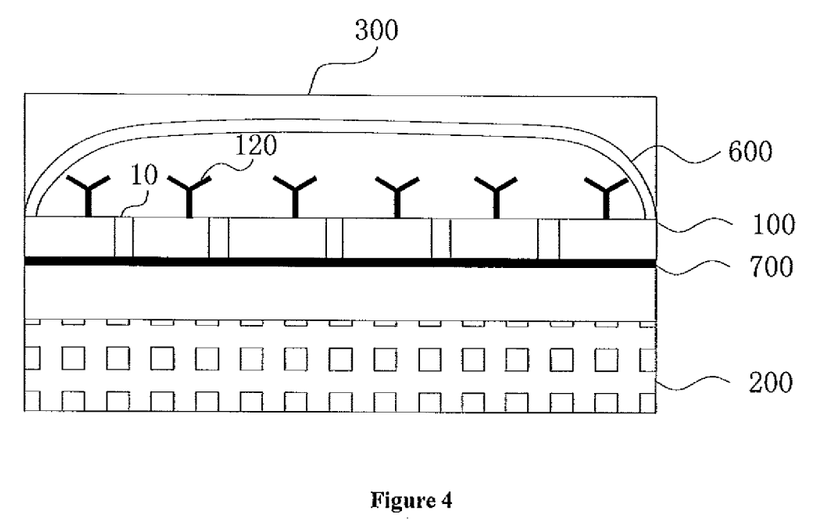
FIG. 4 is a schematic diagram of an exemplary device configuration in accordance with another embodiment of the invention.

In order to improve the lifetime of the device and provide protection of the device and membrane (100) surfaces from contamination, the device may further include an isolation or protection layer (600), a supporting layer (700) or both as shown in FIG. 4. The isolation layer (600) covers the membrane (100) surface, either partially or completely, and is removable to expose the surface of membrane (100) at the time of use. The isolation layer (600) may, thus, be made of any material that protects the surface of the membrane (100) surface and which can readily be removed prior to use of the device. In one embodiment, the isolation layer (600) may be a water-soluble layer, such as a film of poly(acrylic acid), that can be removed by submerging it into an aqueous solution, for example, the sample solution. The isolation layer (600) may also be removed by application of a stimulation, such as an electrical stimulation, e.g. voltage, that dissolves the isolation layer. Thus, the isolation layer (600) may comprise a material that can be electrochemically dissolved, such as a thin gold film. As one of skill in the art will appreciate, there is no limitation to the composition, configuration, or mechanism of removal of the isolation layer.

In order to improve the mechanical properties of the membrane (100), a supporting layer (700) may be included adjacent to the second surface (30) of membrane (100), e.g. the surface opposite to the first membrane surface (40) which includes receptors (120). The supporting layer (700) provides mechanical strength to the membrane (100) and does not interfere with the function of the membrane (100). The supporting layer (700) is, thus, made of an inert material suitable to provide strength to the membrane, for example, a silicon nitride substrate or a filter membrane/paper that may include pores that are preferably larger than the pores of the membrane, e.g. micron-sized pores, so as not to cover the membrane pores and impede passage of the reporter species therethrough.

Figure 5:
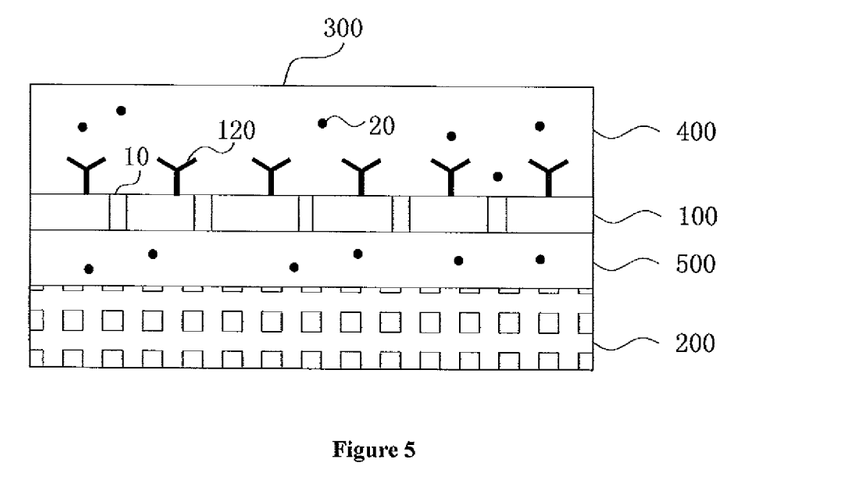
FIG. 5 is a schematic diagram of an exemplary device configuration in accordance with another embodiment of the invention.

Reporter species (20) may be naturally present in the sample solution, as seen in FIG. 5, or added to the sample solution either before or after the sample solution is added to the sample reservoir (400). Typically, for the detection of minute amounts of analyte in a sample, the sample must be concentrated to increase analyte concentration for detection by conventional electrochemical sensors. However, using the present device, the detector (200) is not used to detect the analyte directly. Instead, the detector (200) detects the amount/rate of reporter species (20) that passes through the membrane (100), from the sample reservoir (400) into the detection reservoir (500), and this correlates with the amount of analyte in the sample. Thus, the reporter species (20) is generally present in the sample solution at a high concentration, for example, at mM concentrations, while analyte may be present at concentrations in the picomolar to nanomolar (pM-nM) range. Therefore, the type of detector (200) that may be used in the present device is not restricted, and may include detectors ranging from conventional electrochemical sensors to nanoelectronic sensors. It is also noted that, since analyte concentration is based on the amount of reporter species (20) that passes through the membrane (100), preparation of the sample prior to detection by concentrating analyte in the sample is not required when using the present device.

Figure 6:
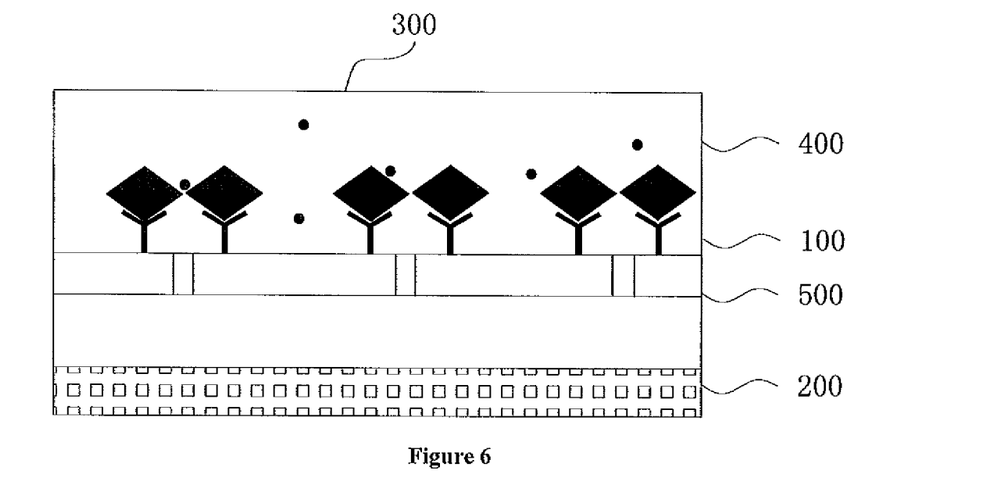
FIG. 6 is a schematic illustration of one exemplary detection method in accordance with an embodiment of the invention.
Figure 7:
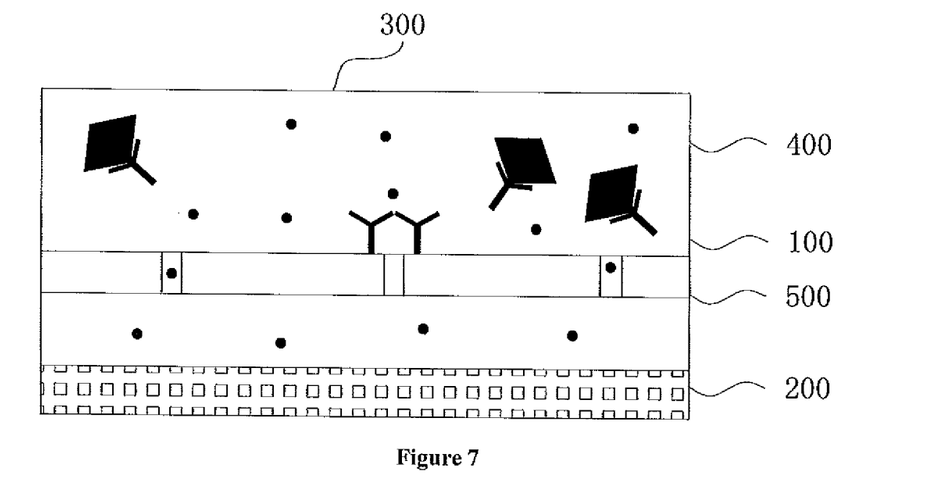
FIG. 7 is a schematic illustration of an exemplary detection method in accordance with another embodiment of the invention.

As set out above, receptor-analyte binding alters the passage of the reporter species across the membrane (100), for example, receptor-analyte binding may either increase or decrease the rate at which reporter species (20) passes through the membrane (100). As shown in FIG. 6, binding of the target analyte (50) to the receptor (120) may result in blocking of part or all of pores (10), thereby inhibiting the passage of reporter species (20) into the detection reservoir (500). For example, when analyte binds to the receptors, a change in the morphology of the receptor, e.g. size and/or shape, blocks the pores, for example, by steric hindrance, or by a change in the charge of the molecules at the pore openings, thereby preventing passage of the reporter species through the membrane pores. This type of gate-keeper membrane is referred to herein as a "negative" membrane (100). Alternatively, as shown in FIG. 7, receptor-analyte binding may increase the rate at which reporter species (20) pass through membrane (100). In this case, receptors are bound to the membrane such that they block the pores and prevent passage of reporter species through the membrane. Receptor-analyte binding results in a change that unblocks the pores and permits passage of reporter species through the pores of the membrane. The change may include release of the receptors (120) from the membrane on binding with analyte, or a change in receptor morphology (e.g. converting DNA receptor from hairpin to straight). This type of gate-keeper membrane is referred to herein as a "positive" membrane.

Overall, the device of the present invention has the following advantages. The present device provides improved sensitivity and lower limits of detection through detection of a reporter species, which can be added to or naturally present in the sample solution at a high concentration, as opposed to direct detection of target analyte which is often present at very low concentrations. As a result, sample preparation to concentrate analyte in the sample is not required. In addition, the use of the gate-keeper membrane prevents exposure of the detector/transducer to the analyte(s) and other substances within the sample solution and thereby prevents undesirable interactions and degradation of the detector. This preserves the intrinsic high sensitivity of transducers, such as nanotubes, nanowires, and nanoplatelets.

Embodiments of the invention are described in the following specific examples, which are not to be construed as limiting.

Example #1—Gate-Keeper Membrane Made of Semi-Aligned Carbon Nanotubes

Vertically-aligned multi-walled carbon nanotubes (MWCNTs) were grown on a silicon base with a 4 nm thick Fe film as the catalyst, as previously reported (Mazloumi et al., ACS Nano, 7, 4281-4288 (2013). The growth was achieved using chemical vapor deposition (CVD) with high purity ethylene as the carbon source, mixed with hydrogen and argon (70:70:70 sccm), in a 25 mm tube furnace (Lindberg) at a growth temperature of 725° C. Ultra-long (~500 µm) and aligned MWCNTs were grown in 1 hour. Growth time can be varied to obtain the desired tube length.

Figure 10:
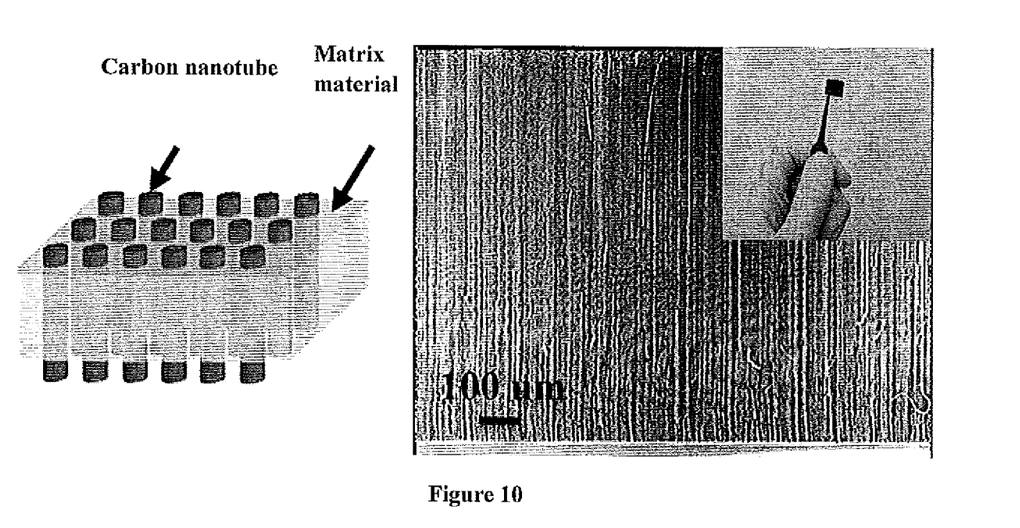
FIG. 10 shows an exemplary gate-keeper membrane substrate made of semi-aligned carbon nanotubes embedded in PDMS.

In order to fabricate the membrane, the MWCNTs were embedded in a polydimethylsiloxane (PDMS, Sylgard 184, 1:10 catalyst:resin ratio) substrate and cured in a vacuum oven for 1 hour at 70° C. (CNT-PDMS) to yield a membrane as shown in FIG. 10. CNT-PDMS membranes were then submerged in HF for 10 minutes to detach them from the silicon base. Following this, the CNT-PDMS membranes were wet etched in a 3:1 solution of N-methyl pyrrolidinone (NMP) and tetra-butyl ammonium fluoride (TBAF) in water for 1.5 hours to chemically etch away excess PDMS. Subsequently, membranes were then exposed to plasma oxidation for 20 minutes to further remove excess polymer from the surface, and open CNT tips.

Example #2—Gate-Keeper Membrane Made of Stacked Graphene Oxide (GO)

Graphene oxide was synthesized using a modified Hummers method, as described in Gao and Tang, Carbon, 76, 133-140 (2014), from natural graphite. Briefly, graphite flakes (3.0 g, 100 mesh, Sigma-Aldrich) and 1.5 g $NaNO_3$ were mixed with 70 mL concentrated $H_2SO_4$, stirred for 30 minutes and transferred to a 0° C. ice bath. Following this, 15.0 g $KMnO_4$ was added slowly to keep the temperature below 20° C. After all the $KMnO_4$ was added, the mixture was heated to 35° C. and mixed for 2 hours. The mixture was carefully diluted with 140 mL deionized (DI) water and stirred for another hour. The flask was then removed from the water bath and the mixture was cooled to room temperature, filtered, and washed several times with 5% HCl and DI water.

A membrane made of stacked GO platelets was then prepared by vacuum filtration of certain volumes of diluted aqueous GO solution (0.1 mg/mL) onto a polycarbonate (PC) substrate.

Example #3—Array of Carbon Nanotube Chemiresistors

An array of carbon nanotube chemiresistors as shown in FIG. 8 was made as described in Tang et al., Physics in Medicine and Biology, 50, N23-N31 (2005). Briefly, to generate an electrode pattern, an $SiO_2$/Si wafer was coated with photo-resistant film and the electrode pattern was produced by deep UV photolithography. Metal (W/Pt) electrodes were then deposited on the wafer by evaporation and liftoff. Single-walled carbon nanotubes (SWNT) were then synthesized by patterned chemical vapor deposition (CVD) as described in Example 1 on top of the W/Pt electrodes.

Example #4—Array of Carbon Nanotube Network Chemiresistors

An array of carbon nanotube network chemiresistors as shown in FIG. 9 was made as follows. A single-walled carbon nanotube (SWNT) network was prepared by synthesizing a sub-monolayer of SWNTs using chemical vapour deposition (CVD), as described in Example 1. Briefly, catalyst solutions were made by dissolving fumed silica, iron (III) acetylacetonate, molybdenum (II) acetate and cobalt (II) acetate in ethanol followed by a 2 hour sonication. This solution was then spin coated onto a piranha (3:1 of $H_2SO_4:H_2O_2$) cleaned Si/2 µm $SiO_2$ wafer. The wafer was then placed into a 2 inch quartz tube CVD chamber in a high purity argon (1200 sccm) and hydrogen (36 sccm) environment. The temperature was then ramped to the growth temperature of 850° C. Once the growth temperature was reached the flow of gas was diverted through an ethanol bubbler held at 1° C. for 20 minutes. The bubbler was then bypassed and the chamber was allowed to cool to room temperature.

SWNT network transfer, patterning, and cleaning was conducted as follows. Polymethylmethacrylate (PMMA) films were spin coated (3000 rpm) onto the SWNT network for mechanical and optical support during transfer. The network was subsequently immersed in HF acid to dissolve $SiO_2$ as well as the catalyst particles beneath the SWNT network. Liftoff occurs once the network is carefully placed in water, where the SWNT network floats to the water's surface due to surface tension and the SWNT's hydrophobicity.

Device substrates were fabricated using conventional photolithography and liftoff on p++ Si/50 nm $SiO_2$ for deposition of titanium/gold (5 nm/50 nm) electrodes. The substrates have 32 electrode pairs with a 150 µm device length and varying device widths. The device widths used include 100 µm, 50 µm, 25 µm and 10 µm, with 8 devices at each width. The SWNTs were aligned and transferred onto the electrode arrays and dried with a nitrogen gun. Remaining water was evaporated in a vacuum oven at 120° C. for an hour. The PMMA was gently removed in an acetone bath. SWNT patterning involved using conventional photolithography to protect the film between each set of electrodes. The substrate was subsequently plasma etched at 20 mTorr and 100 W oxygen plasma for 5 minutes. The SWNT network was then cleaned using an 8 hour soak in 170° C. dimethyl sulfoxide (DMSO). The final device array is shown in FIG. 9.

Example #5—DNA Sensor Using the Semi-Aligned CNT Membrane Coupled with an Electrochemical (E-Chem) Transducer A gate-keeper CNT membrane (110) was prepared as described in Example 1. Receptor DNA (120) was embedded into the membrane as follows. A conjugation reaction was carried out at room temperature using carbodiimide chemistry with a final volume of 1 mL containing 10 µM amino-modified probe DNA (Cy3-T15-NH2), 10 mM EDC.HCl (freshly prepared), 25 mM NaCl, and 25 mM MES (pH 6.0). The CNT-ssDNA complex was purified by removing the solution and washing the membrane with deionized water twice to remove free ssDNA. T15 is 15 thymine residues.

Figure 11:
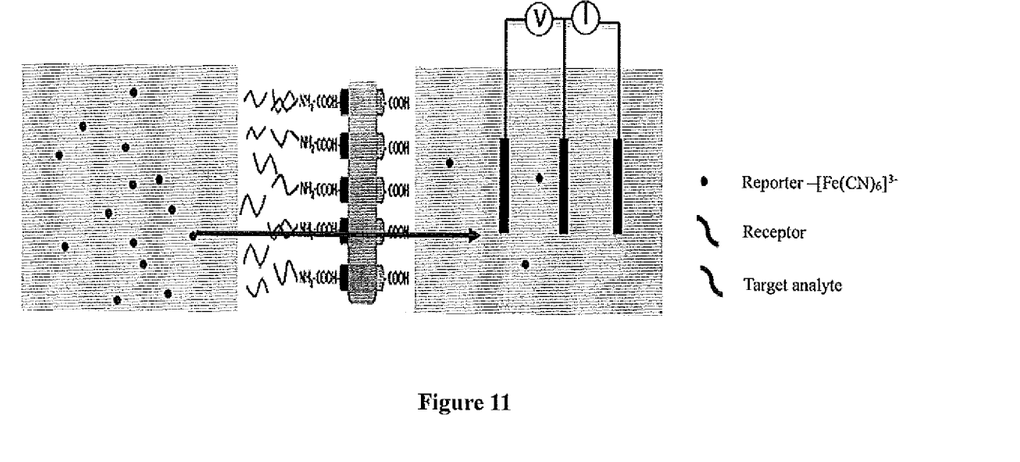
FIG. 11 is a schematic illustration of the detection process in accordance with an embodiment of the invention.

The ssDNA-CNT membrane was then sandwiched between two additional PDMS O-rings and polystyrene (PS) cuvettes, which functioned as the sample and detection reservoirs (400 & 500), respectively. The reservoirs were both filled with 0.1M KCl electrolyte solution (1 mL in feed and 2 mL in permeate). An E-chem transducer comprising three electrodes (work, counter, and reference) was placed in the detector reservoir. Sample with target analyte (400 pM A15 ssDNA) (0.5 mL) was mixed with 0.5 mL of the detector (1 M $[Fe(CN)_6]^{3-}$), and added to the sample reservoir as shown in FIG. 11. A15 is 15 adenine residues. A reference device incorporating a CNT membrane with no receptor DNA, and a control device comprising a PDMS membrane without CNT pores and without receptor DNA were also prepared.

Figure 12:
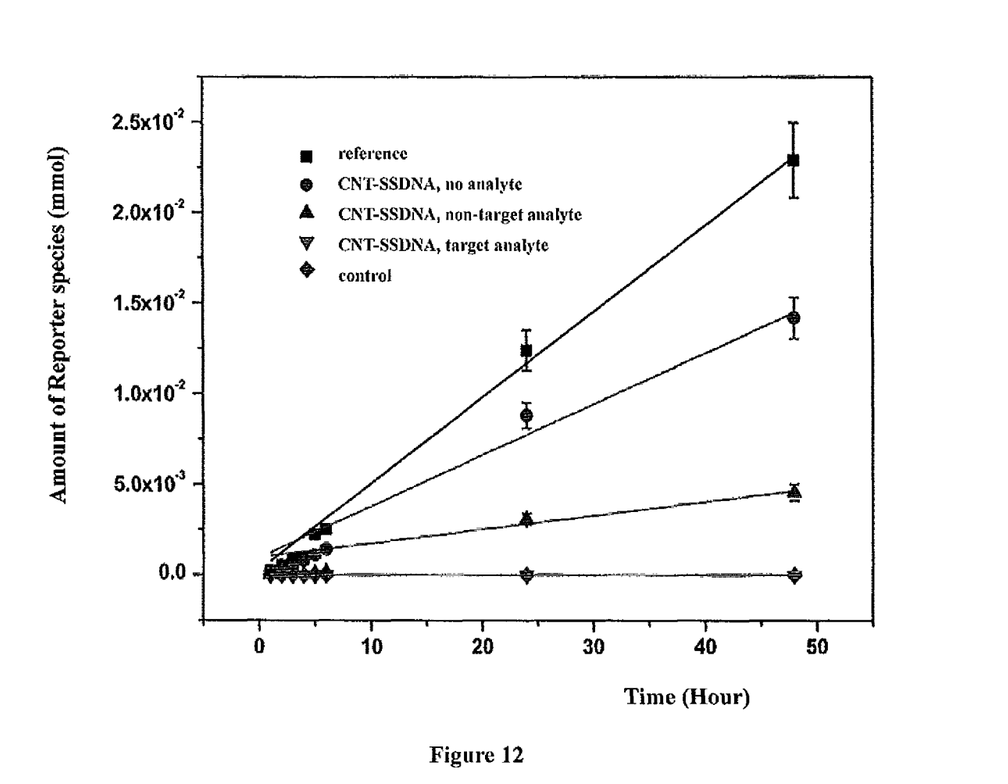
FIG. 12 graphically illustrates the electrochemical measurement of a reporter species in accordance with the detection process of FIG. 11.

The E-chem transducer readout using each device was monitored to determine flow of detector from the sample reservoir into the detection reservoir in the absence of analyte. The test results are shown in FIG. 12. The slopes of the lines shown in FIG. 12 is the flow rate of $[Fe(CN)_6]^{3-}$ across the gate-keeper membrane. For the reference device (plain CNT membrane, no receptors), $[Fe(CN)_6]^{3-}$ ions pass freely through the CNT pores from the sample reservoir to the detection reservoir as there is no receptor-analyte binding to block the pores. Therefore, the slope (i.e. translocation or flow rate) is the highest. For the control device (PDMS, no CNT), $[Fe(CN)_6]^{3-}$ ions cannot pass through the membrane since there are no pores on the membrane. Therefore, the slope (i.e. flow rate) is zero. For the CNT-ssDNA membrane, the slope (i.e. flow rate) is reduced compared to reference membrane, indicating partial blockage of the CNT pores by the ssDNA (receptors) anchored at the pore entrances. In the presence of target analyte, the flow of the $[Fe(CN)_6]^{3-}$ ions across the CNT-ssDNA membrane is not detectable. The slope (i.e. flow rate) is zero indicating that hybridization of the receptor ssDNA and the target analyte ssDNA completely blocked the CNT pores. On the other hand, in the presence of non-target analyte, for example, a single-base mismatched ssDNA (AAAAAAAC AAAAAAA), translocation of the $[Fe(CN)_6]^{3-}$ ions across the CNT-ssDNA membrane slowed down but was significantly higher than that in the presence of target ssDNA, indicating that mismatched ssDNA only block part of the CNT pores. This result demonstrates the high sensitivity and specificity of the device.

The invention claimed is:

1. A device for the detection of a target analyte in solution, said device comprising:
   a sample reservoir comprising a reporter, and a detection reservoir;
   a gate-keeper membrane comprising a substrate having a first receptor surface for exposure to a target analyte in the sample reservoir, and a second opposing surface exposed to the detection reservoir, wherein the substrate is adapted to incorporate pores sufficient to permit passage of the reporter through the gate-keeper membrane from the sample reservoir into the detection reservoir;
   one or more analyte-specific receptors anchored on the first receptor surface of the substrate which bind with the target analyte, wherein binding of the one or more analyte-specific receptors with the target analyte prevents passage of the target analyte and biomolecules through the pores of the gate-keeper membrane into the detection reservoir and alters the passage of the reporter through the pores of the gate-keeper membrane, wherein binding of the target analyte to the one or more analyte-specific receptors opens the pores to permit passage of the reporter through the gate-keeper membrane or closes the pores to prevent passage of the reporter through the gate-keeper membrane and wherein the amount of target analyte correlates with the change in the amount of reporter that passes through the gate-keeper membrane to permit detection of the target analyte without exposure of the target analyte to a detector; and one or more detectors in the detection reservoir which interact with the reporter that passes through the gate-keeper membrane from the sample reservoir to the detection reservoir, said one or more detectors adapted to emit a detectable signal that permits quantification of the change in the amount of the reporter in the detection reservoir, wherein said device does not have a detector in the sample reservoir exposed to the target analyte.

2. The device of claim 1, wherein the gate-keeper membrane is within an enclosure, and divides the enclosure into the sample reservoir and the detection reservoir.

3. The device of claim 1, wherein the substrate is selected from polydimethylsiloxane (PDMS), epoxy, polyethylene glycol (PEG), hydroxypropyl cellulose (HPC), poly(N-isopropylacrylamide), silica nanoparticles, iron oxide nanoparticles, and alumina nanoparticles.

4. The device of claim 1, wherein the pores are micro- or nano-sized pores formed by carbon nanotubes, graphene or graphene oxide.

5. The device of claim 1, wherein the gate-keeper membrane comprises a supporting layer to provide mechanical strength to the gate-keeper membrane.

6. The device of claim 5, wherein the supporting layer is formed of porous silicon nitride or a filter membrane.

7. The device of claim 1, comprising a removable protective layer which partially or completely covers the gate-keeper membrane and is removed before use of the device.

8. The device of claim 7, wherein the protective layer is water-soluble or removable by applying an electric potential.

9. The device of claim 1, wherein the receptor is selected from the group consisting of nucleic acid, aptamers, antibodies, peptides and enzymes.

10. The device of claim 9, wherein the receptor is anchored on the gate-keeper membrane by covalent linkage, electrostatic attraction, ionic bonding, hydrogen bonding, or van der Waals' forces.

11. The device of claim 1, wherein the one or more detectors are electrochemical detectors.

12. The device of claim 11, wherein the one or more detectors are two or more microelectrodes, one or more field effect transistors, or one or more carbon nanotube chemiresistors.

13. The device of claim 1, wherein the one or more detectors emit a detectable signal selected from current, voltage, potential, or impedance.

14. The device of claim 1, wherein the reporter is selected from a mobile ion, a redox species, an oxidizing agent, or a reducing agent that induces an event that is electrochemically detectable.

15. A method for detecting a target analyte in a sample comprising the steps of:

i) adding the sample into a sample reservoir of a detection device comprising:

a sample reservoir, and a detection reservoir;

a gate-keeper membrane comprising a substrate having a first receptor surface for exposure to a target analyte in the sample reservoir, and a second opposing surface exposed to the detection reservoir, wherein the substrate is adapted to incorporate pores sufficient to permit passage of a reporter through the gate-keeper membrane from the sample reservoir into the detection reservoir;

one or more analyte-specific receptors anchored on the first receptor surface of the substrate which bind with the target analyte, wherein binding of the one or more analyte-specific receptors with the target analyte prevents passage of the target analyte and biomolecules through the pores of the gate-keeper membrane into the detection reservoir and alters the passage of the reporter through the pores of the gate-keeper membrane, and wherein the amount of target analyte correlates with the change in the amount of reporter that passes through the gate-keeper membrane to permit detection of the target analyte without exposure of the target analyte to a detector; and one or more detectors in the detection reservoir which interact with the reporter that passes through the gate-keeper membrane from the sample reservoir to the detection reservoir, said one or more detectors adapted to emit a detectable signal that permits quantification of the change in the amount of the reporter in the detection reservoir, wherein said device does not have a detector in the sample reservoir exposed to the target analyte, wherein the sample or the sample reservoir comprises a reporter; and ii) detecting analyte in the sample based on a detector signal that indicates a change in the amount of the reporter passing through the gate-keeper membrane from the sample reservoir to the detection reservoir.

16. The method of claim 15, wherein the substrate is selected from polydimethylsiloxane (PDMS), epoxy, polyethylene glycol (PEG), hydroxypropyl cellulose (HPC), poly(N-isopropylacrylamide), silica nanoparticles, iron oxide nanoparticles, and alumina nanoparticles, the pores are micro- or nano-sized pores formed by carbon nanotubes, graphene or graphene oxide, and the receptor is selected from the group consisting of nucleic acid, aptamers, antibodies, peptides and enzymes.

17. The method of claim 15, wherein the one or more detectors comprise two or more microelectrodes, one or more field effect transistors, or one or more carbon nanotube chemiresistors and the detectable signal emitted by the detector is selected from current, voltage, potential, or impedance.

* * * * *